United States Patent [19]

Borsanyi et al.

[11] Patent Number: 5,098,377
[45] Date of Patent: Mar. 24, 1992

[54] MULTIMODAL DISPLACEMENT PUMP AND DISSOLUTION SYSTEM FOR SAME

[75] Inventors: Alexander Borsanyi, Newport Beach; Richard Harp, La Costa; Robert Lebo, Silverado; Scott L. Pool, Santa Ana; Joseph Rondinone, Mission Viejo; John T. Sorensen, Costa Mesa; Roxanne Wall, Newport Beach; Albert L. Stone, Laguna Hills, all of Calif.

[73] Assignee: Baxter International Inc., Deerfield, Ill.

[21] Appl. No.: 559,124

[22] Filed: Jul. 26, 1990

Related U.S. Application Data

[63] Continuation-in-part of Ser. No. 240,992, Sep. 6, 1988, abandoned.

[51] Int. Cl.⁵ .............................................. A61M 1/00
[52] U.S. Cl. ..................................... 604/30; 604/151; 604/319
[58] Field of Search ....................... 604/4-6, 604/27-35, 49, 51, 118-120, 131, 151-153, 257, 319; 128/DIG. 12; 417/394, 472, 473

[56] References Cited

U.S. PATENT DOCUMENTS

| | | | |
|---|---|---|---|
| 3,142,299 | 7/1964 | Henderson | 604/34 |
| 3,543,752 | 12/1970 | Hesse et al. | 604/152 X |
| 3,545,438 | 12/1970 | DeVries | 604/28 |
| 3,570,488 | 3/1971 | Diskin et al. | 604/31 |
| 3,592,183 | 7/1971 | Watkins et al. | 604/28 X |
| 3,730,183 | 5/1973 | Goldsmith et al. | 604/29 |
| 3,841,331 | 10/1974 | Wilder . | |
| 3,932,065 | 1/1976 | Ginsberg et al. | 417/317 |
| 4,065,230 | 12/1977 | Gezari | 417/317 |
| 4,276,023 | 6/1981 | Phillips et al. | 433/85 |
| 4,315,506 | 2/1982 | Kayser et al. | 604/28 |
| 4,327,724 | 5/1982 | Birk etal. | 604/152 X |
| 4,421,464 | 12/1983 | Schmidt et al. | 417/412 |
| 4,479,761 | 10/1984 | Bilstad et al. | 417/395 |
| 4,483,665 | 11/1984 | Hauser | 417/401 |
| 4,548,550 | 10/1985 | Tsuji | 417/390 |
| 4,583,920 | 4/1986 | Lindner | 417/266 |
| 4,604,037 | 8/1986 | Hoya | 417/394 |
| 4,655,690 | 4/1987 | Boedecker et al. | 417/53 |
| 4,655,744 | 4/1987 | Thistle et al. | 604/28 |
| 4,723,941 | 2/1988 | Thistle et al. | 604/152 |
| 4,755,168 | 7/1988 | Romanelli et al. | 604/34 |
| 5,000,739 | 3/1991 | Kulisz et al. | 604/132 |
| 5,047,012 | 9/1991 | Leuschner et al. | 604/32 |

FOREIGN PATENT DOCUMENTS

| | | |
|---|---|---|
| 73862 | 12/1987 | Australia . |
| 0278689 | 8/1988 | European Pat. Off. . |
| 2009864 | 6/1979 | United Kingdom . |

Primary Examiner—John D. Yasko
Assistant Examiner—Adam J. Cermak
Attorney, Agent, or Firm—Sandra S. Schultz; June M. Bostich; Robert D. Buyan

[57] ABSTRACT

Disclosed is a pneumatically-driven volume controlled bellows pump apparatus for oscillating liquid into a localized area of the human body, preferably methyl-tertiary butyl ether or another solvent, into the gallbladder. The pump includes a fluid reservoir in the form of an inverted syringe attached via a stopcock to the bellows. The bellows is attached via a second stopcock to a catheter also attached to a priming syringe. An inlet pinch valve is disposed between the bellows and the fluid reservoir and an outlet pinch valve between the bellows and the fluid receiver.

To use the pump, a pigtail catheter with outlets in the pigtail is inserted into the desired area of the body, preferably a receptacle such as the gallbladder, to introduce a selected volume of liquid for gallstone dissolution. Liquid is infused into the receptacle by decompression of the bellows with the inlet but not the outlet valve open and then by compression of the bellows with the outlet but not the inlet valve open. Repeated infusion and aspiration is automatically accomplished by decompression and compression of the bellows with the inlet valve closed and the outlet valve open, or by compression and decompression of the bellows while the inlet valve is open and the outlet valve is closed alternated with compression and decompression while the inlet valve is closed and the outlet valve is open. Complete aspiration is accomplished by the use of a vacuum pump attached to the fluid reservoir. Also disclosed are syringe units and a transfer cap for use with the pump, together with a method for dissolving gallstones.

35 Claims, 9 Drawing Sheets

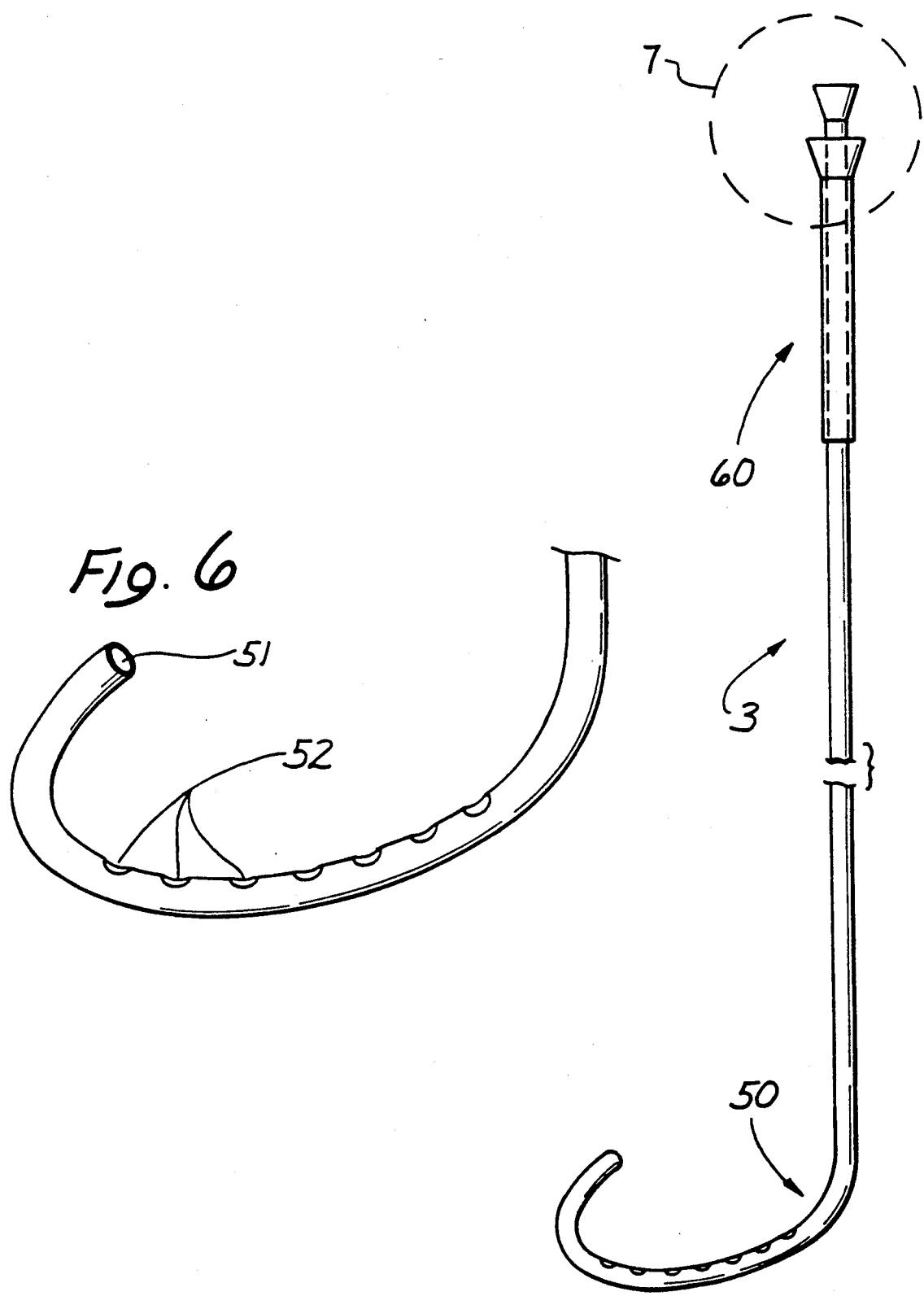

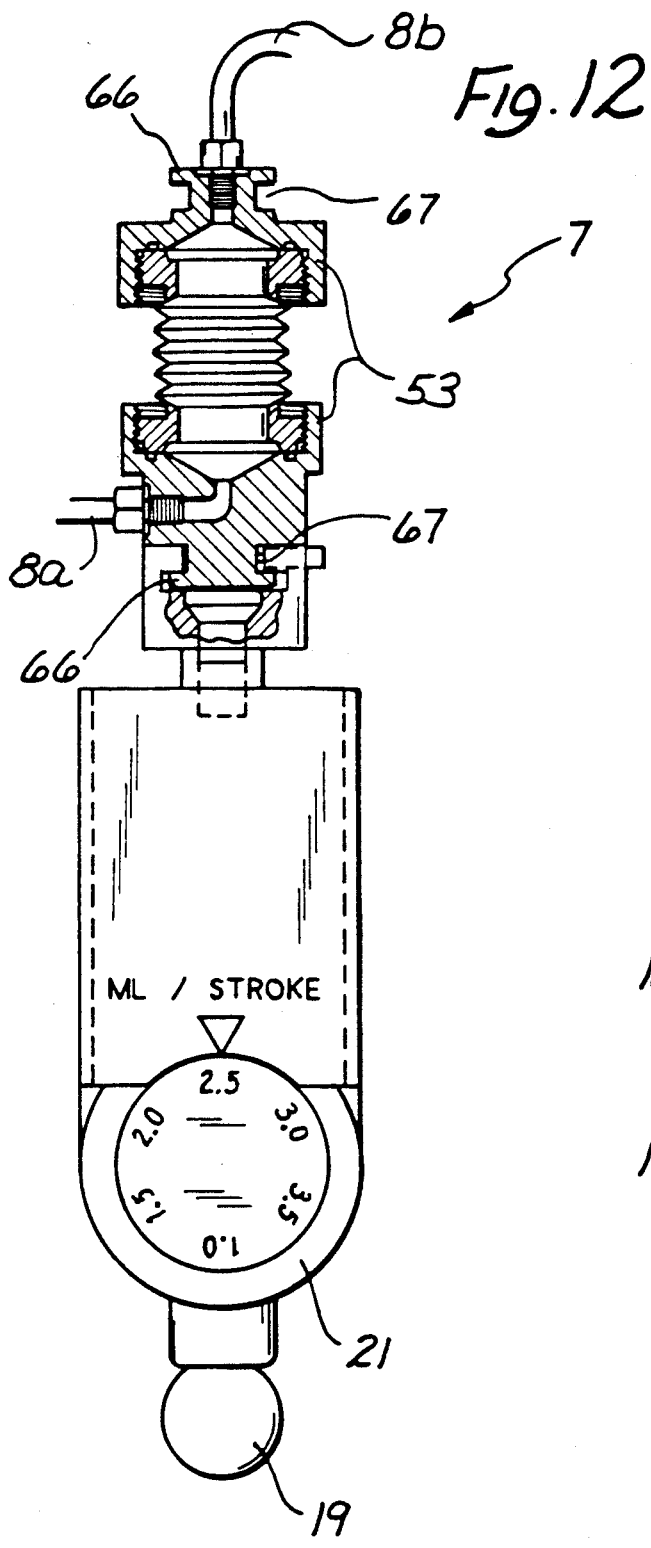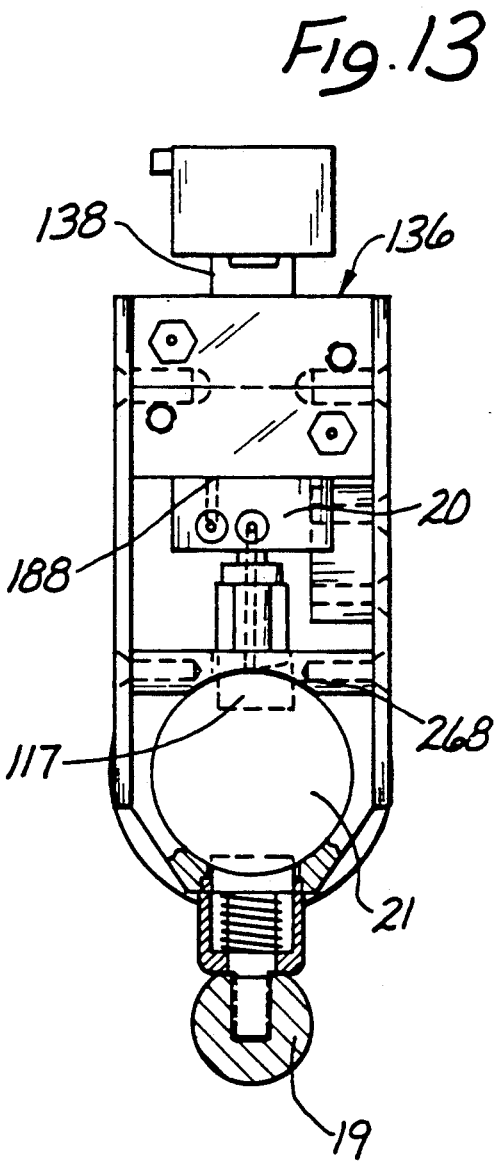
Fig. 12
Fig. 13

MULTIMODAL DISPLACEMENT PUMP AND DISSOLUTION SYSTEM FOR SAME

This application is a continuation-in-part of U.S. Patent application Ser. No. 240,992, filed Sept. 6, 1988, now abandoned.

BACKGROUND OF THE INVENTION

1. Field of the Invention

This invention relates to pumps, particularly pumps for introducing fluids into the human body, as well as syringes, bottle caps and the like for use in connection with such pumps for gallstone dissolution and the like.

2. Description of the Prior Art

Solidified masses such as biliary duct stones and gallstones may develop in hollow organs or ducts within humans and animals and cause numerous health problems, as is known to those skilled in the art. These deposits may be removed from the body in various ways, including surgery or in vivo dissolution by solvents introduced into the localized area of the body, such as the gallbladder, where the stones are located.

In order to effectively dissolve stones such as gallstones in vivo, however, an effective means of introducing and distributing the fluid is necessary; agitation of the fluid is advantageous and speeds up the dissolution process substantially; it can be accomplished by repeatedly cycling or oscillating the fluid into and out from the body area of interest. Furthermore, an effective dissolving agent is necessary; monooctanoin, for example, can be used, and methyl tertiary-butyl ether ("MTBE"), for example, has been found to be very effective, but is quite flammable. Moreover, while MTBE is non-toxic so long as it remains confined to the gallbladder, it is highly toxic if supplied in sufficient volume to cause leakage from the biliary duct into the surrounding tissues.

Any apparatus for injecting and aspirating MTBE, therefore, would advantageously include safety features designed to limit either the pressure of fluids within the body cavity or the volume of fluid injected therein and would be constructed of materials not degraded or dissolved by the solvent. In addition, to avoid fire, the pump and control system should be such that the solvent is never exposed to electrical spark.

Pumps have been designed for use in such dissolution systems. For example, in U.S. Pat. No. 4,723,941, a piston pump is disclosed for oscillating methyl tertiary-butyl ether ("MTBE") and other solvents into the gallbladder. In U.S. Pat. No. 4,655,744, another pump is disclosed which provides a fluid trap between the gallbladder and the pump to remove the bile. However, an effective flexible but simple closed system pump with minimal air leakage and with optimum handling of all functions desirable in a dissolution pump has not previously been developed.

Other pumps having multimodal operation have been designed for various applications, such as that described in U.S. Pat. No. 3,382,811, but require several displacement mechanisms and are designed to provide a constant output flow in the mainstream output line.

SUMMARY OF THE INVENTION

The present invention includes infusion apparatus and related accessories particularly suited for gallstone dissolution, although useful for other purposes as well.

The preferred embodiment is a volume control pump apparatus which provides multiple modes of operation (i.e. infusion, aspiration, oscillation, and the like) useful for in vivo gallstone dissolution. In the preferred embodiment, air leakage into the pump system and the gallbladder is eliminated by the design of the unit, and strict control of the volume of solvent in the gallbladder is maintained. Furthermore, the preferred control system, a pneumatic logic module operating the unit, minimizes any fire hazard associated with the use of electricity and includes a vacuum fill feature that safeguards against inadvertently filling the gallbladder.

The invention in one aspect is an apparatus for transferring a variable selected volume of fluid, said apparatus having a fluid source, a transfer means for transferring fluid to or from the fluid source and a fluid receiver, a first means for closing off fluid flow from the source to the transfer means, and a second means for closing off fluid flow from the transfer means to the receiver. A pneumatic control means including a vacuum source independently controls the transfer means and the first and the second closing means so that a preselected volume of fluid can be transferred from the fluid source to the fluid receiver and vice versa, at the user's selection, while avoiding the risk of forcing an excessive amount of fluid into the fluid receiver as could result from use of positive pressure for transferring the fluid.

In preferred embodiments, the control means also functions to oscillate the preselected volume of fluid between the transfer means and the fluid receiver, at the user's selection. In addition the fluid source is preferably a refillable syringe within an air-tight chamber and the control means includes means for emptying the contents of the fluid source into a waste receptacle and for refilling the source from a source reservoir.

Preferably, the transfer means is a positive displacement means, most preferably a bellows pump, and the fluid source is a vertically aligned syringe with a graduated barrel situated uppermost so that fluid output and input can be measured. The first and second closing means are preferably pinch valves closed by air cylinder pistons controlled by the pneumatic logic.

It is critical to this invention that the volume of fluid delivered by the stroke of the positive displacement transfer means be adjustably variable so that the user can select an exact amount of fluid to be delivered to the fluid receiver. For instance, in a bellows pump, the length of the bellows stroke is adjustably variable to control the volume of liquid infused or withdrawn. Further, the transfer means and the vacuum source, i.e. the bellows pump and the reservoir syringe, are both vertically aligned and designed so that the lighter phase of a two phase fluid will be differentially transferred to the fluid receiver, while the heavier phase will be differentially retained within the transfer means and/or the fluid source, depending upon the mode of operation selected. In the preferred use, bile withdrawn from the gallbladder under treatment will be differentially transferred to the fluid source rather than retained in the bellows, and MTBE containing dissolved gallstone can be reinfused into the gallbladder or exchanged depending on whether it has become saturated with the solute. As the apparatus is designed, the control system opens and closes the inlet and outlet valves so that the bellows, on extending and compressing, withdraws fluid from the fluid source and infuses it into the fluid receiver. During an oscillation cycle, the control system provides means for manipulating the valves such that the fluid infused into the fluid receiver can be rapidly and repeatedly withdrawn and reinfused for a preselected period of time. Preferably, the fluid receiver is a gallbladder reached via a catheter. Alternatively, all valves can be opened and the bellows compressed while fluid is aspirated directly from the fluid receiver to the fluid source via a vacuum applied to the fluid source.

In another aspect, the invention includes a cap for a fluid container comprising a cap unit and tubing, the tubing disposed to extend through the cap unit into the container at one end and terminating in a luer seal at the other to facilitate withdrawal of liquid from the bottle by syringe.

Finally, the invention in another aspect also includes a method utilizing the apparatus of the invention for dissolving solidified masses in a localized area or cavity of the body, such as the gallbladder, by infusing a given volume of fluid solvent into said localized area and oscillating a smaller volume to and from said localized area to dissolve said masses therein. Preferably, for dissolution of gallstones the solvent used is methyl tertiary-butyl ether, although other solvents such as monooctanoin can be used.

BRIEF DESCRIPTION OF THE DRAWINGS

FIGS. 5 and 6 are side elevations of the preferred catheter to be used with the pump of the present invention.

FIGS. 12 and 13 are, respectively, a front elevation of the volume selection mechanism, the bellows, and the bellows drive piston and a side elevation of the bellows control mechanism in the preferred pump.

DESCRIPTION OF THE SPECIFIC EMBODIMENTS

The present pump may have many uses, but is particularly effective for use in gallstone dissolution, wherein the gallbladder is the fluid receiver and the pump infuses and withdraws liquid therefrom. For gallstone dissolution, the fluid is preferably methyl tertiary-butyl ether, although it can be another solvent such as monoctanoin or any subsequently discovered solvent or solvent system.

Figure 1:
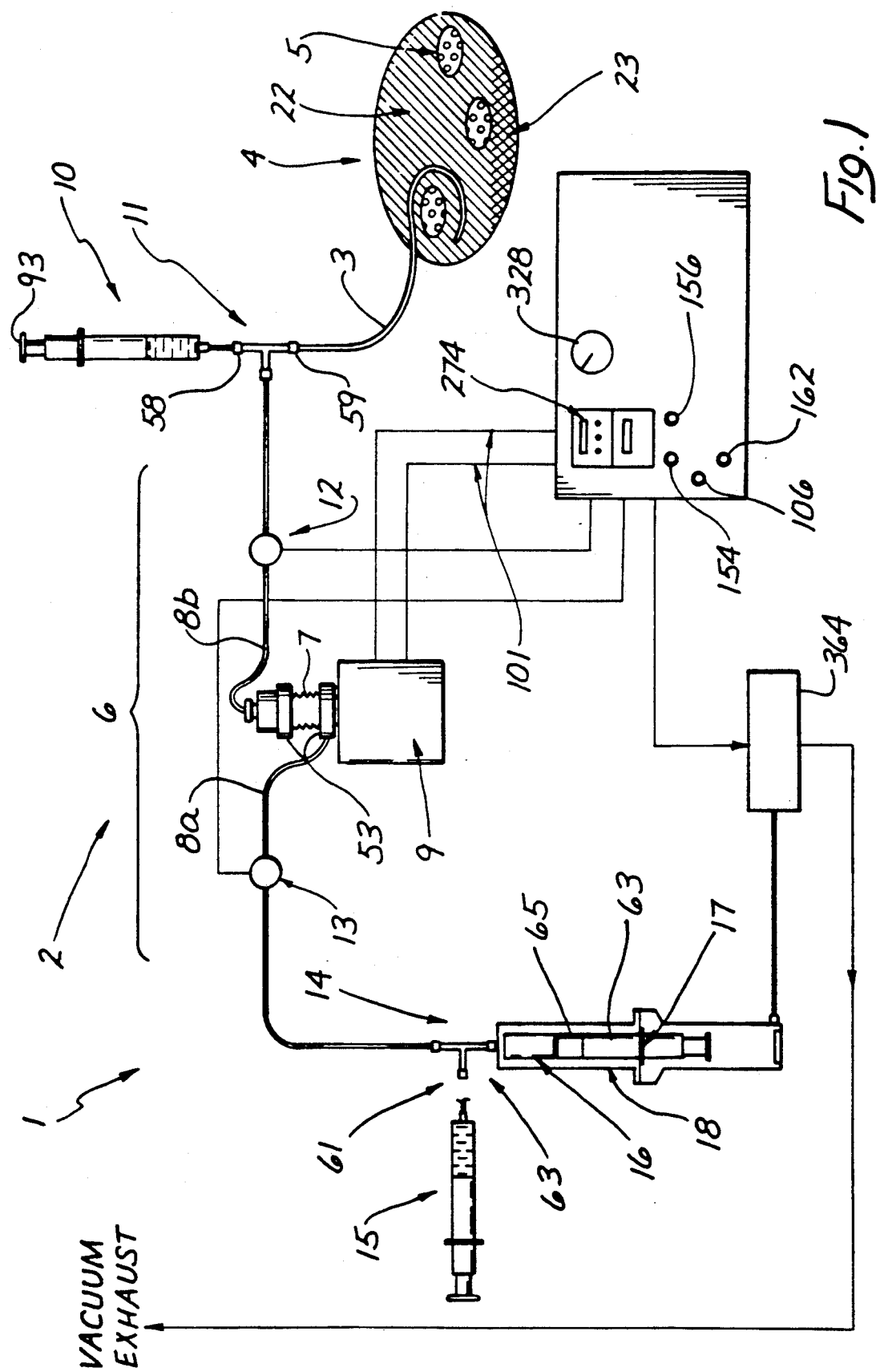
FIG. 1 is a schematic diagram of one embodiment of the pump system.
Figure 2:
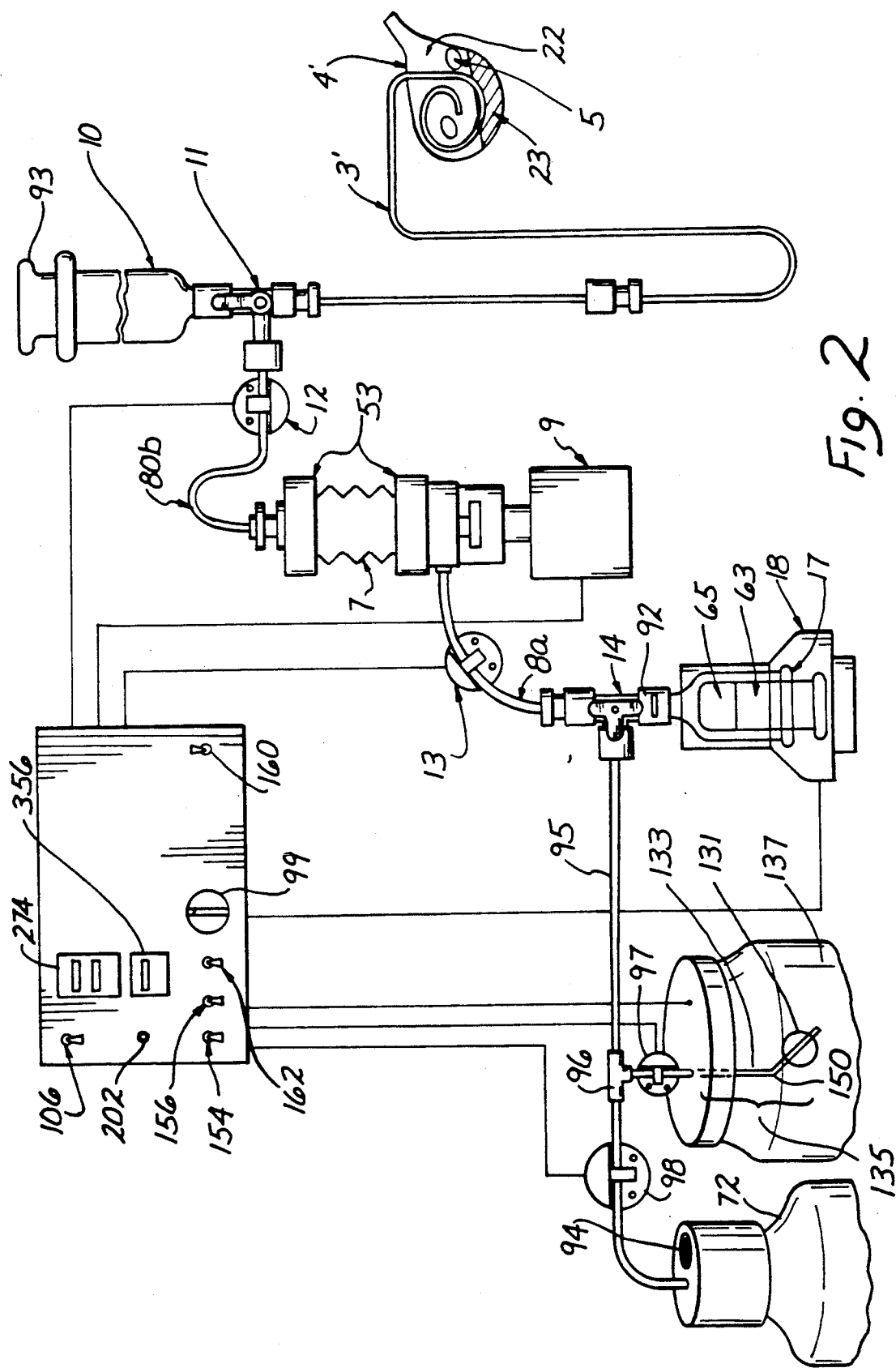
FIG. 2 is a schematic diagram of the preferred pump system.

The system 1, as shown in FIGS. 1 and 2, includes a single-lumen disposable catheter 3 which can be used independent of pump 2. It is shown in detail in FIGS. 5 and 6 and includes a pigtail 50 with an opening 51 at the far end plus fluid outlets 52 disposed along the inside length of the pigtail. When in use with the pump, the catheter 3 is attached via a threaded luer lock 59 (shown in FIG. 7) to stopcock 11 in the upper corner of the pump. The catheter includes a sheath 60 surrounding the catheter at the upper end to prevent crimping or occlusion.

Figure 3:
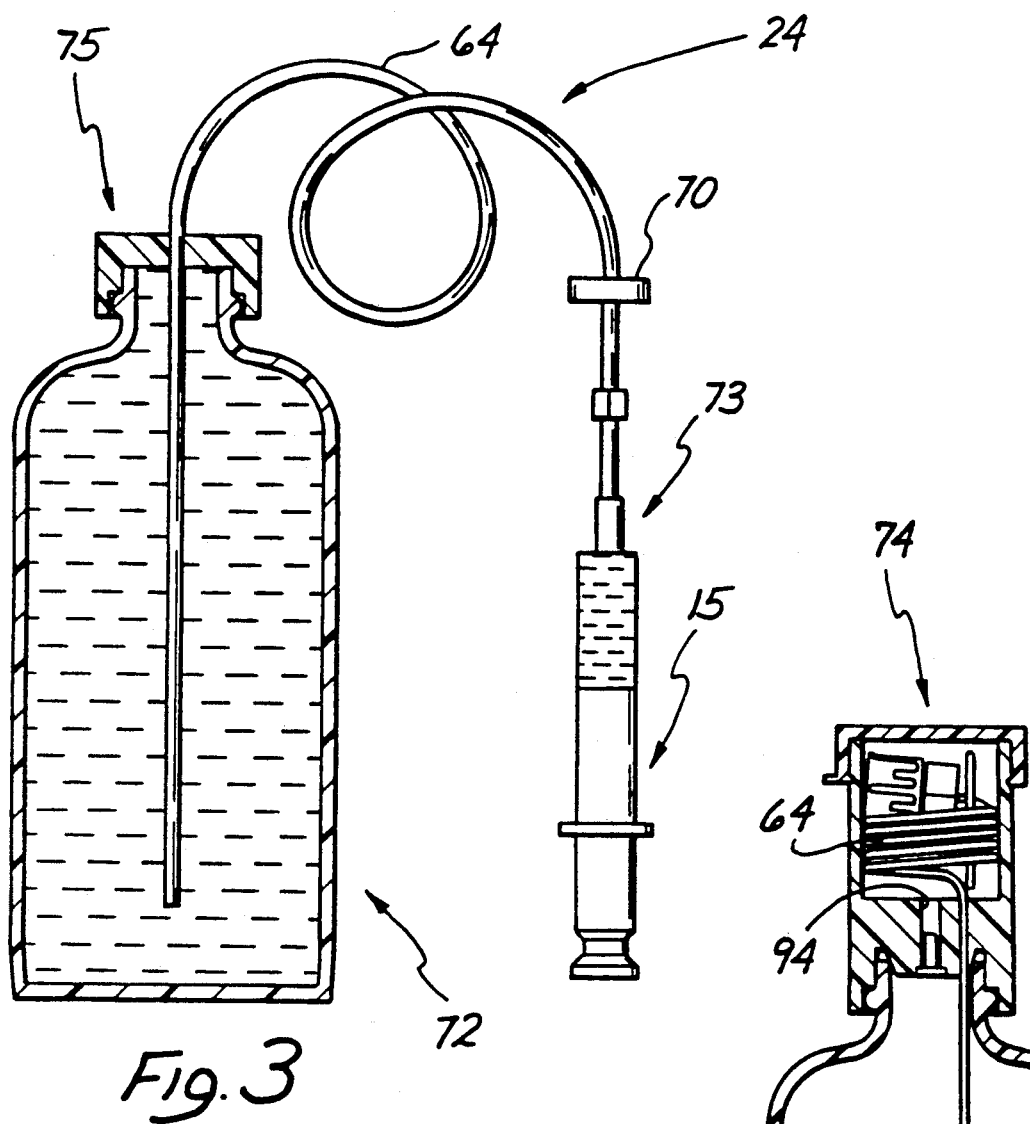
FIGS. 3 and 4 are cross sections of the preferred MTBE containers and transfer caps of the system of the present invention.
Figure 4:
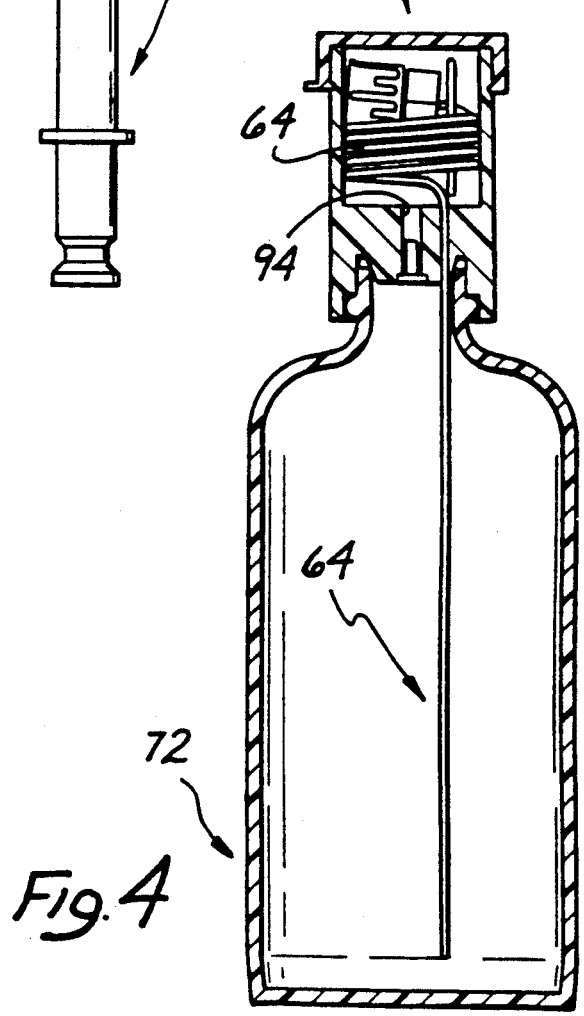

A transfer cap 24 shown in FIG. 3 is also provided as part of the system 1. It consists of a bottle cap 75 (for a bottle 72 of MTBE) having conduit 64, preferably a flexible plastic tubing, passing therethrough and terminating in a luer lock 73. Input syringes 15 for input of MTBE into the pump can be attached to the luer lock to be quickly filled with MTBE in a sterile fashion. The syringe can then be capped and the transfer cap closed off, for example by a slide clamp 70. As shown in FIG. 4, transfer cap 24 can include a removable, sealable cap 74 at the top of bottle cap 75 which contains helically wound tubing 64. Alternatively, and preferably, bottle 72 can be placed into direct fluid communication with reservoir 16 of reservoir syringe 17 by attaching the end of tubing 64 extending from bottle 72 directly to luer lock 61 and vacuum means 364, such as a vacuum pump, can be used to withdraw plunger 63 and thereby draw fluid from bottle 72 into reservoir 16.

Returning to the pump 2, stopcock 11 is attached via another luer lock 58 to a standard 50 milliliter syringe 10 which is sealed off by the stopcock when the pump is in use. It is also attached to conduit 8b of treatment set 6. Preferably treatment set 6 is a sterilizable, disposable unit comprising conduit 8b, a disposable positive displacement transfer means (preferably a disposable flexible plastic bellows 7) and conduit 8a. Treatment set 6 is illustrated in FIGS. 1 and 2, and in more detail in FIGS. 9-11.

Bellows 7 is made of a flexible, compressible, material such as polypropylene. Other materials such as teflon, nylon, and polyethylene can be used, but must be essentially impervious to the fluid being pumped. Use of a bellows as the positive displacement means is particularly desirable when the pump is used for gallstone dissolution because it is very reliable and provides a completely sealed system without the possibility of air leakage inherent in a piston unit, for example.

Figure 9:
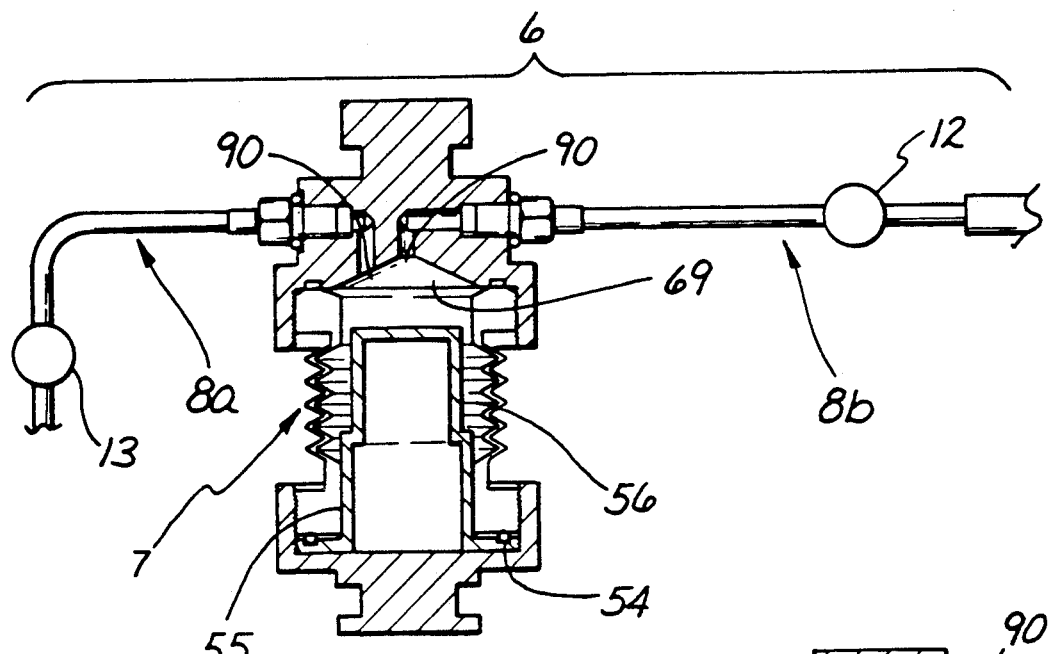
FIGS. 9, 10 and are cross-sections of several embodiments of the bellows and transfer set of the preferred pump of the present invention.
Figure 10:
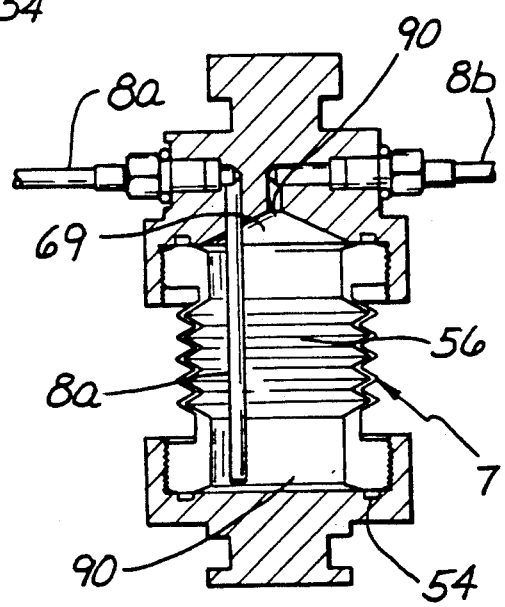
Figure 11:
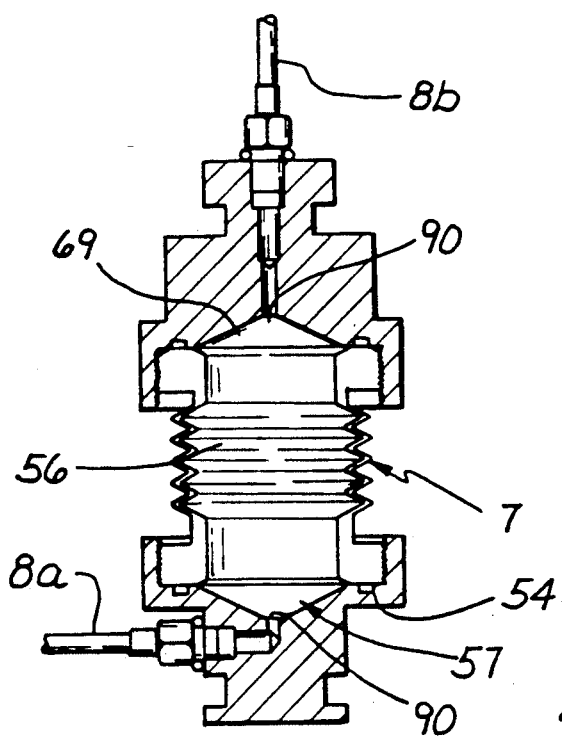

As shown in FIG. 12, treatment set 6 containing bellows 7 terminates at the top and bottom in rigid bases 53 which extend to caps 66 via necks 67. Bellows 7 and bases 53 form a bellows chamber 56 as shown in FIGS. 9, 10 and 11. Inlet and outlet ports 90 are incorporated within caps 53. Necks 67 are configured so that the bellows unit can be suspended in place on the pump by fastening means not shown in the drawings. In the preferred embodiment, the bellows holds from about ½ to 20, most preferably ½ to 7, milliliters in bellows chamber 56 in its compressed position.

Figure 14:
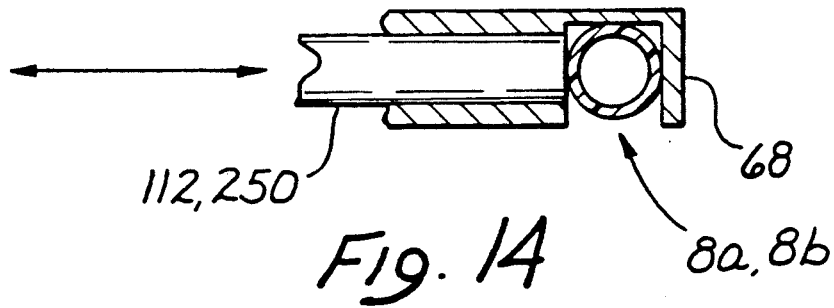
FIG. 14 is a cross-section of the preferred pinch valve operating mechanism of the present invention.
Figure 15:
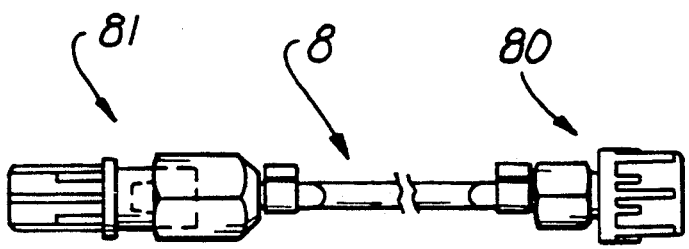
FIG. 15 is a front elevation of the luer lock connectors of the present invention, connecting the preferred disposable transfer set to the rest of the preferred pump.

Conduit 8, preferably made of nylon or another relatively MTBE-impervious polymer tubing, extends from ports 90 in bases 53 of transfer set 6 on each side to withdraw and add fluid to the bellows chamber 56. Conduit 8, section 8b, passes through outlet valve 12, preferably a pinch valve, while section 8a passes through inlet valve 13, also preferably a pinch valve. As shown in FIG. 14, both valves have a surface post 68, so that tubing 8 can be compressed against it by a piston 112 or 250 (operated by the fluid logic of the pump as described later) to close the valve by closing off the tubing. It should be noted that in FIGS. 16-17, the valve pistons 112 and 250 are shown schematically as moving "upward" and "downward," and are referred to as such. In actual operation, however, they are aligned and move horizontally in order to compress the tubing against post 68.

The bellows 7 are compressed when in "home" position; compression and extension are activated by a pneumatic logic system 9 positioned below the bellows and extending behind the pump; connecting tubing 101 is shown on FIG. 1.

As shown in FIG. 9, in one embodiment, the bellows includes a displacement cup 55 to absorb some of its volume; however, the bellows is preferably used without the displacement cup because the larger fluid volume in bellows chamber 56 appears more desirable. (The larger volume of MTBE used without the displacement cup has an increased capacity for holding solute (cholesterol) before reaching saturation. This allows longer treatment periods between exchanges of solvent.)

Conduit 8a and 8b exit from the top of the bellows chamber 56 which is conical (69) at its upper end. In the embodiment shown in FIG. 10, conduit 8a extends adjacent the bottom of bellows chamber 56; as a result, when the bellows compresses, it differentially withdraws liquid at the lower portion of the chamber. Thus when MTBE (shown as 22 in gallbladder 4) and bile (shown as 23 in gallbladder 4) mix in chamber 56 (the bile settling at the bottom and the MTBE remaining at the top), bile is differentially withdrawn from bellows chamber 56 by conduit 8a and transferred to reservoir 16 in reservoir syringe 17 while MTBE is differentially withdrawn from the top of bellows chamber 56 and transferred to gallbladder 4.

In the preferred embodiment shown in FIG. 11, bellows chamber 56 terminates at its lower end in a cone 57 and conduit 8a exits directly from the bottom also differentially withdrawing bile.

Figure 16:
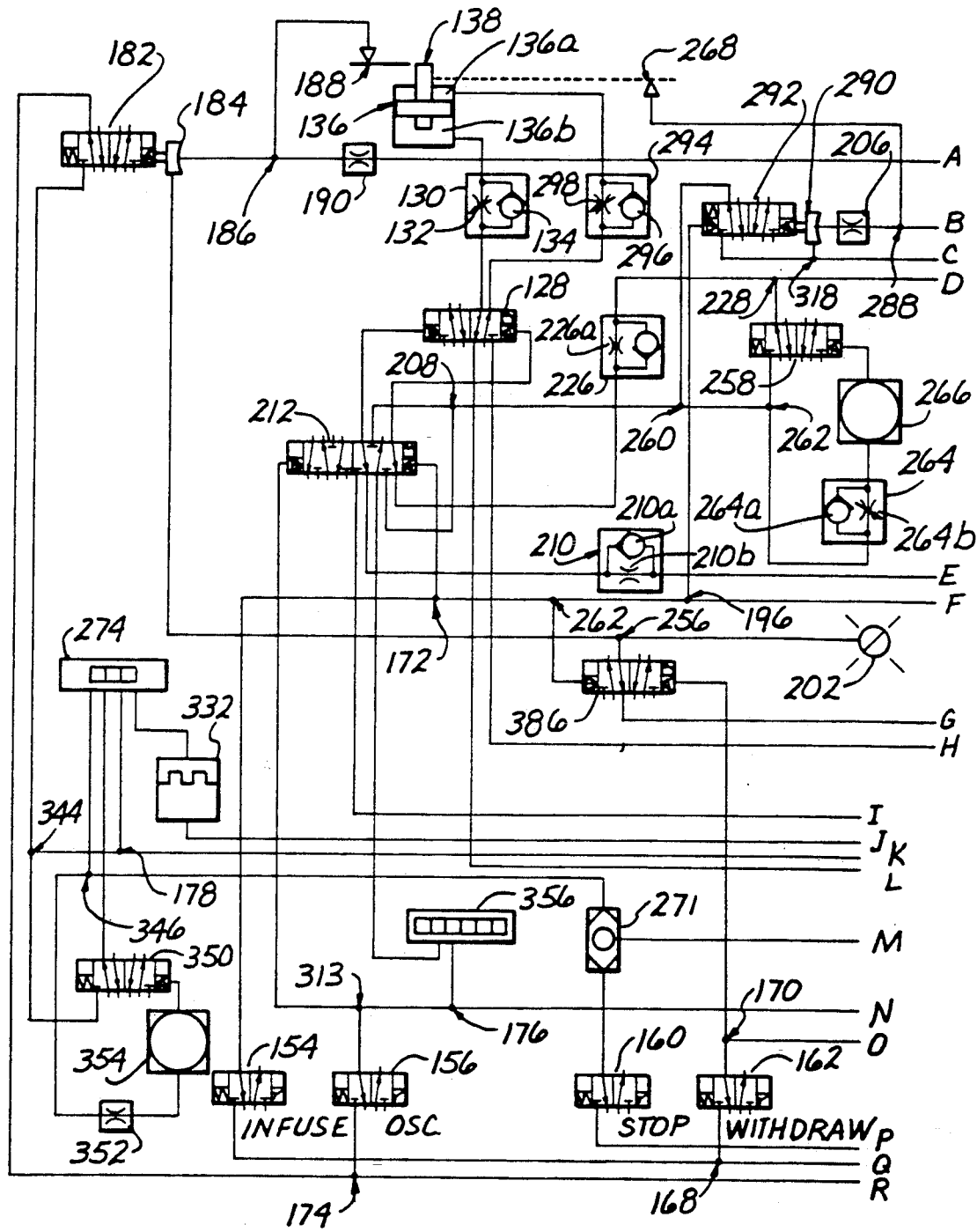
FIGS. 16, and 17 are the left and right portions of the schematic covering the preferred pneumatic logic system operating the pump.

Disposable bellows 7 rests atop bellows drive cylinder 136 as shown in FIGS. 12, 13 and 16. Air supplied to the bellows drive cylinder can drive piston 138 upward or downward, thus either compressing or extending the bellows 7. Also attached to piston 138 is a sensor port 20 which moves in unison with bellows 7. The uppermost position of piston 138 is limited when sensor port 20 contacts the bottom of bellows drive cylinder 136. The consequent sealing the orifice of the top sensor 188 is detected by the logic circuit 9. The bottommost position of piston 138 is limited by sensor port 20 meeting stroke adjust wheel 21. Upon contact, the orifice for the bottom sensor 268 is occluded, thus transferring a signal to pneumatic logic circuit 9 as described hereinafter. The location of this lower stop may be selected by the user retracting wheel lock 19 to release stroke adjust wheel 21 and rotating wheel 21 to one of six positions. Each of these positions correlates to a specific stroke volume output as marked on the stroke adjustment wheel 21. Wheel lock 19 is then released to re-engage it and prevent inadvertent changes to the stroke adjustment. This mechanism allows the user to choose a stroke volume suitable to the patient's anatomy.

Figure 7:
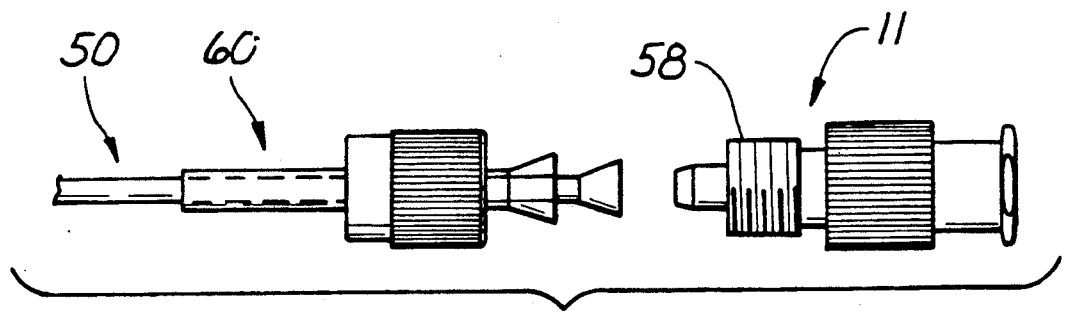
FIG. 7 is a front elevation of the threaded luer lock connecting to the catheter.
Figure 8:
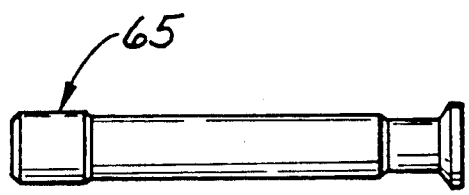
FIG. 8 is a front elevation of the plunger of the reservoir syringe of the preferred pump.

Conduit 8a is attached (via a connection as shown in FIG. 7) to stopcock 14. In one embodiment, stopcock 14 is in turn attached via side luer lock 61 to input syringe 15, preferably a 30 milliliter standard syringe for injecting fluid into reservoir syringe reservoir 16. Stopcock 14 seals off input syringe 15 when not in use, and attaches via a lower luer lock 92 to reservoir syringe reservoir 16. Reservoir syringe 17, for example a 20-50 milliliter syringe, contains a plunger 63 which provides a seal with barrel 64 along only a portion, preferably along tip 65, of its length, to minimize a tendency of the piston 63 to become immobile due to crystallization of cholesterol in the MTBE where the piston seals.

Main reservoir 16 is held in sealed chamber 18 attached to vacuum means 364, for example a Bernouilli's venturi. When the vacuum is activated during the withdraw cycle of the pump, piston 63 of reservoir 16 is drawn downward to withdraw liquid from the rest of the system into the reservoir. Because syringe 16 is volumetrically graduated, the exact amount of liquid going into and coming out of the system can be tracked and controlled.

The pump can be controlled by a number of different means known in the art, such as an electrical system, a microprocessor, a mechanical, or a hydraulic system. Software can be provided to program the sequence of events. However, in the preferred embodiment, fluid, preferably air or pneumatic logic is used as the control system because it eliminates any fire hazard from the use of electricity or the like where MTBE is used. Furthermore, most hospitals have an air supply in each room so that the use of pneumatic logic is convenient; even if there is no such air supply, air or nitrogen, being compressible, is convenient to keep and handle compared to liquid cylinders for hydraulic systems, for example, which would require large storage areas.

Figure 17:
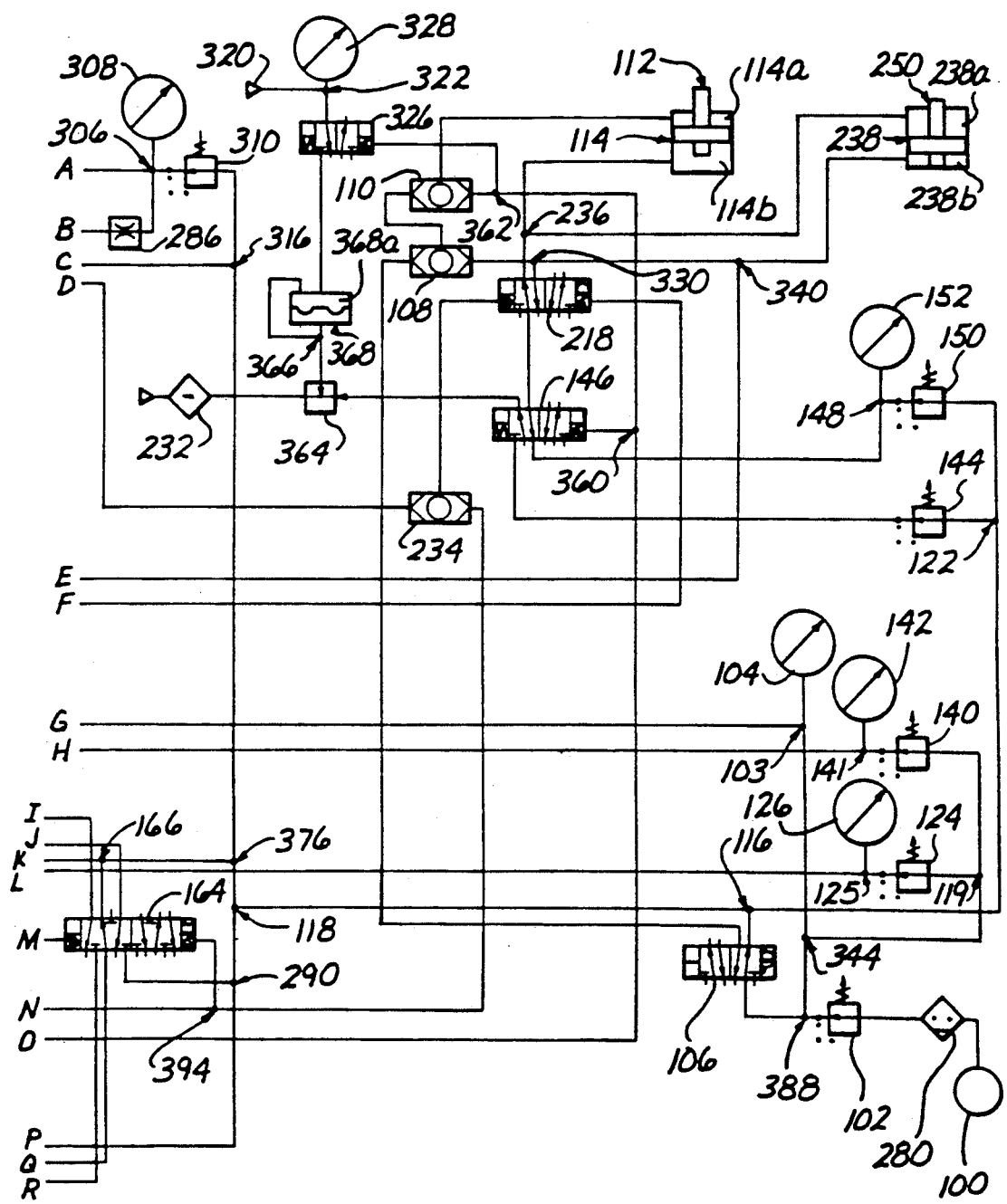

The entire preferred air logic system is shown in FIGS. 16-17. A cylinder 100 of compressed air or nitrogen provides a pressure flow through the system. Alternately, an air compressor or other non-flammable gas source can be used. Air signals pass through the logic system to control the pump. The majority of the system is connected by tubing 101 of polyurethane, although other polymer or nonpolymer materials can be used. Individual components of the system such as valves, OR gates, sensors, and the like are generally made of aluminum, stainless steel, or teflon in the preferred system.

Air from cylinder 100 passes through filter 280, then regulator 102 at a pressure controlled by the operator, passes by pressure gauge 104 which provides a readout of input pressure and from there into run/prime toggle valve 106. From junction 119, the signal passes through regulator 124 (set by the user) and pressure gauge 126 to provide a constant input signal to the bellows home valve 128, a detented pressure-piloted valve of the type well known in the art. Also from junction 119, the signal passes through regulator 140 and pressure gauge 142 to bellows home valve 128 to provide a constant input signal thereto.

Air from regulator 124 is deflected and exits valve 128 to variable flow control device 130 having a check valve 134 and a variable restricted orifice 132 to regulate flow. Air exiting from flow control device 130 passes into lower chamber 136b of bellows drive cylinder 136 to force bellows drive piston 138 upwards to "home" position whereby the bellows is compressed.

The run/prime valve is a detented toggle valve which can be purchased off the shelf and is known in the art. In essence, it is the power switch for the system. This toggle valve, like all toggle valves, contains in essence two port configurations and toggles between them so that the user activates one or the other configuration depending on the position of the toggle switch.

Because this is a "detented" toggle valve, when the user flips the switch to one position or the other, the valve remains in the new position until re-toggled to the other position.

In the prime mode, the inlet pinch valve is open and the bellows drive cylinder is extended. When toggled to "prime" or "off" position B, the air signal exits the run/prime valve to OR gate 108, OR gate 110, and inlet pinch valve control cylinder 114, upper segment 114a thereof, to force inlet pinch valve drive piston 112 downward to open inlet valve 13 as described via FIG. 14. This allows the entire system to be primed before use because both the inlet valve 13 and the outlet valve 12 (which remains in "home" position, i.e. open, as described later) are open.

Run/prime valve 106 when toggled to the "run" position activates portion A of the valve. In run position, the inlet pinch valve is closed, the outlet pinch valve is open, the bellows drive cylinder is extended and the supply reservoir vacuum chamber is vented to the atmosphere. To accomplish this, the air signal passes through the system as follows. It passes through junction 116 and then in turn through junctions 118, and 122.

From junction 122, the signal passes through regulator 144 to vacuum enable valve 146, a spring-return pressure piloted valve known in the art, to provide a constant input thereto. From junction 122, also, the signal passes through regulator 150 and pressure gauge 152 to vacuum enable valve 146, to provide constant input thereto when the system is in run mode. Vacuum enable valve 146 in default position passes the signal from regulator 150 to pinch state valve 218, a detented pressure-piloted valve.

Pinch state valve 218, is left in B or "home" position after previous operation of the pump; as a result, the air from regulator 150 exits valve 218 to junction 236 to upper portion 238a of outlet pinch valve cylinder 238 and to lower portion 114b of inlet pinch valve cylinder 114 to force the outlet pinch valve piston 250 downward to "home" position to open the outlet valve and to force the inlet pinch valve piston 112 upward to "home" position to close the inlet valve.

Also from junction 118, an air signal passes to junctions 166, 178, 290, 316, 318, 344 and 376. These junctions pressurize valves 164, 160, 182, 292, and 350. In addition, junction 178 provides constant input to the seconds remaining counter 274, and junction 180 provides input into up relay valve 182, a spring-return pressure piloted valve and provides input to or receives output from "up amplifier" diaphragm 184, also an off-the-shelf unit known in the art.

From junction 316, a signal also passes through sensor regulator 310, pressure gauge 308, and junction 306. From junction 306, the two sensors, 268 and 188, are pressurized. Bottom sensor 268 is pressurized via a restricted orifice flow control device 286 which restricts the flow to junction 288 and from there to sensor 268 as well as down amplifier 290 via restrictor 206. The function of sensor 268, of course, is to sense when bellows drive piston 138 is at the bottom of its cycle and the bellows themselves extended, in order to activate upward piston movement and resulting bellows compression.

Similarly, top sensor 188 is pressurized from junction 306 via restricted orifice flow control device 190 and junction 186. Junction 186 also provides pressure to or allows back flow from sensor 188 to up amplifier 184.

Top sensor 188 is designed to sense when the bellows drive piston 138 is at its uppermost position and the bellows compressed to activate downward piston movement and extension of the bellows.

Once priming of the pump is complete, thus, and the pump is to be used, the run/prime valve is toggled to run position which puts the pump in an initial home position as described above and which provides constant input as described above into certain valves of the system.

During the infusion cycle, the inlet valve opens, the outlet valve closes, and the bellows drive cylinder retracts, thus filling the bellows with fluid from the reservoir, the valves simultaneously change state back to home position and the bellows drive cylinder extends, forcing the fluid into the patient. Activating the infusion valve 154, a momentary toggle valve, initially provides a signal to junction 172. The infusion sequence will be described below in numbered steps.

11. From junction 172, the signal passes to junctions 262 and 196. Junction 172 supplies air to the A pilot of valve 212, junction 196 supplies air to the B pilot of valve 292, and junction 262 supplies air to the B pilot of valve 386. Also junction 196 supplies air to the A pilot of valve 218. The former valves are detented pressure-piloted valves.

12. Valve 386, now B piloted, allows a signal to pass to patient infused indicator 202 and up amplifier 184 via junction 256. With the pinch valve state valve 218 A piloted, air is now supplied to junction 330 while junction 236 is vented to the atmosphere. The signal divides at 330 through OR gate 108, through OR gate 110 and into the upper chamber 114a of the inlet pinch valve 114, thus driving its piston 112 down to open the pinch valve jaws. The signal from 330 also passes junction 340 to the lower chamber 238b of the outlet pinch valve air cylinder 238, driving its piston 250 up, thus closing the jaws of pinch valve 12. Air from junction 340 now passes through the restriction orifice 210b of restrictor 210. It continues to valve 212, which as stated above has been A piloted.

13. The restricted signal passing through 210 is diverted through valve 212 and finally reaches the B pilot of valve 128. This causes air to pass through valve 128 from regulator 140 to speed control 294 then into the upper portion 136a of bellows drive air cylinder 136, thus forcing piston 138 down at a rate selected by the operator using the variable restrictor 298.

14. When piston 138 reaches the end of its stroke, which is also adjustable by the user, sensor orifice 268 is occluded. Since air supplied to junction 288 can no longer escape via the sensor, the pressure begins to increase. This pressure is monitored by amplifier 290, an off-the-shelf item known in the art, which in turn triggers the A pilot of valve 292.

15. Input air supplied to valve 292 may now pass to valves 212 and 258 and to variable flow control 264 via junctions 208, 260 and 262. Since valve 212 is A piloted, as stated above, none of these signals pass valve 212. The signal does, however, pass through flow control 264 at an adjustable rate and begin filling chamber 266, until it surpasses the threshold pressure of the A pilot of valve 258.

16. With valve 258 now A piloted, air may pass to junction 228. A signal now may travel to OR gate 234 and on to the B pilot of valve 218. This returns the pinch valves to their "home" state by allowing air to pass to junction 236. From junction 236, air fills lower chamber 114b of the inlet pinch valve cylinder 114 and upper chamber 238a of outlet pinch valve cylinder 238, thus closing the first and opening the second. Junction 228 also delivers a signal to fixed flow control 226.

I7. Restricted air from the orifice 226a of fixed flow control 226 enters valve 212 and is there directed to the A pilot of valve 128. Once valve 128 is A piloted, air may pass from regulator 124 to variable flow control 130 and into the lower chamber 136b of the bellows drive air cylinder 136. This forces piston 138 up at a rate selected by the user with variable restricted orifice 132.

In the oscillation cycle, the following actions take place: the cycles counter 356 is reset to zero and increments by one for each bellows stroke, the seconds remaining counter begins decrementing once each second, the bellows drive cylinder repeatedly retracts and then extends until the pre-set number of seconds are reached, then the seconds remaining counter resets to its preset number, and the unit returns to the home position. The oscillation cycle is activated by momentary toggle valve 156.

O1. The signal from toggle valve 156 is distributed to the B pilot of valve 212, the A pilot of valve 164, through OR gate 234 and into the B pilot of valve 218, and to the reset input of the cycles counter 356 via junctions 313, 176, and 394. Air to the B pilot of valve 218 assures that the pinch valves are in their "home" state (i.e., inlet pinch closed and outlet pinch open). Air to the reset of cycles counter 356 simply sets its display to zero. With valve 164 A-piloted, a signal can pass to the input of seconds generator 332, which in turn outputs a metered pulse every second to the count input of the seconds remaining counter 274, which decrements its display one count each time a pulse is received. The seconds counter and seconds remaining display are both off-the-shelf components known in the art. Another signal, originating at amplifier valve 182 now is directed through valve 164, through B-piloted valve 212 and to valve 128 so as to set the B pilot thereof.

O2. The B-piloting of valve 128 causes the bellows drive cylinder to retract by supplying air to the upper portion of cylinder 136a. When the sensor port 20 (FIG. 13) engages stroke adjust wheel 21, sensor 268 is occluded.

O3. Pressure supplied to junction 288 increases until it is sensed by amplifier 290, which in turn sets the A pilot of valve 292. This directs a signal to junctions 260, 262, and 208. Junction 208 delivers two signals to valve 212, which is again B-piloted. One of these signals passes to the count input of the cycles counter 356 and causes its display to increment by one. The other signal from junction 208 passes valve 212 to the A pilot of valve 128.

O4. Setting the A pilot of valve 128 supplies air to lower portion 136b of bellows drive cylinder 136, forcing its piston 138 to extend.

O5. Upon full extension of the bellows drive cylinder, upper position sensor 188 is occluded. Air supplied to junction 186 causes a pressure increase that is detected by amplifier 184, which in turn sets the A pilot of valve 182.

O6. A signal now passes through A-piloted valve 182, back through valve 164, through valve 212 and from thence into the B pilot of valve 128 so that steps O2 through O5 above are repeated until the seconds remaining counter 274 decrements from its user-selected value to zero. At the zero reading, the counter outputs a signal that branches at junction 346 to fixed orifice 352 and OR gate 271. The signal passes through orifice 352 and begins filling chamber 354 until the pressure therein surpasses the threshold of the A pilot for valve 350, at which occurrence a signal passes through valve 350 and into the reset input of the seconds counter 274. A reset simply returns the seconds counter to the value selected by the user. The signal at OR gate 271 continues to the B pilot of valve 164, thereby preventing air from passing to the seconds generator 332 and to the B pilot of valve 128. As a result, the pump unit stops with the bellows drive cylinder extended.

To stop the device in an emergency situation, stop valve 160, a momentary toggle valve is toggled, sending a signal via OR gate 271 to activate the B or "off" mode of valve 164. Upon extension of the bellows drive piston, the top sensor 188 is tripped. A signal passes through top sensor enable valve 182 to valve 164 via junction 174 to restore home position by halting the bellows drive.

To withdraw fluid from the gallbladder back to the fluid reservoir, withdraw valve 162, a momentary toggle valve is manually toggled. A vacuum is created in the reservoir chamber, the inlet valve opens, and the patient infused indicator turns off. This result is accomplished in the following steps. A signal passes to junctions 170, 360 and 362 and to OR gate 110 and pressurizes chamber 113a of the inlet pinch valve 114, thus opening the valve.

From junction 360, the A or "on" mode of the vacuum enable valve 146 is activated. From junction 362, the signal passes to the A or "not vented" mode of vacuum chamber vent valve 326, a momentary pressure-piloted valve. A constant input pressure can now exit from valve 146 to an off-the-shelf vacuum means 364.

Vacuum is drawn at junction 366 from upper chamber 368a of diaphragm 368, from junction 322 measured by gauge 328. Diaphragm 368 acts as a safety mechanism during the withdraw cycle; if occlusion or the like occurs in filter 232, it prevents positive pressure from building up in the vacuum system. (If a positive pressure is supplied, for whatever reason, to the inlet port of diaphragm 368, the diaphragm moves to occlude flow to its outlet, thus preventing positive pressures downstream. Only when a vacuum is supplied to its input will it allow flow.) This vacuum is delivered to the vacuum chamber 18, which draws down plunger 63 of reservoir syringe 17 so that fluid is aspirated from the patient's gallbladder.

To use the pump, the patient is first taken to radiology. Catheter 3 is inserted while the patient is in radiology, and the pigtail is settled around the gallstones 5 in the gallbladder 4. Bile (23, see FIG. 1) is aspirated through the catheter, and imaging solution is then injected into the gallbladder until the gallbladder appears full. The gallbladder will continue to fill with bile during the period of treatment. Therefore, to prevent overfilling and leakage of MTBE or other solvent from the gallbladder during the treatment, the amount of imaging solution used to fill the gallbladder is preferably recorded and the amount of solvent used during the dissolution procedure is generally selected to be about half the recorded amount. For example, if eight milliliters are used to fill the gallbladder with imaging solution, approximately four milliliters of solvent will be infused into the gallbladder and then infused and aspirated repeatedly during the oscillation cycle to create turbulence. In some circumstances, a smaller amount can be oscillated. Once the catheter has been placed in the gallbladder, it is usually left in place and used with the pump 2 for the gallstone dissolution process.

To prepare the pump system, all the needed syringes 15 are filled with MTBE using the transfer cap 24 and empty syringes 10 are provided and attached to the system. MTBE is injected from input syringe 15 into the reservoir 16. Alternatively, as shown in FIG. 2, bottle 72, usually having sufficient capacity to refill reservoir 16 of the reservoir syringe a number of times, is attached via port 61 of stopcock 14 and tubing 95 to waste bottle 137 so as to receive aliquots of withdrawn solvent saturated with dissolved cholesterol during the withdrawal phase, as described below.

In use, plunger 93 of syringe 10 is manually withdrawn to prime the bellows and tubings with MTBE and aspirate therefrom any air. Syringe 10 is then sealed off by manually closing stopcock 11. Syringe 10 can also be used to accomplish hand infusion and oscillation of solvent, if necessary, but is normally left sealed off while infusion and oscillation are accomplished under the direction of the pneumatic control system as describe above. The operation of the control system described above is activated by the user toggling run/-prime valve 106 to run position A.

The proper amount of MTBE (approximately four milliliters in this case) is infused to the gallbladder from the reservoir. This is accomplished by hand-selecting the appropriate volume with the stroke adjust wheel 21 and by extension of the bellows with the valves in not home position. The valves are then placed in home position and the MTBE injected into the gallbladder by compression of the bellows to the home position. In the preferred embodiment, all of this is accomplished by pressing the infusion toggle 156 on the pump as described above.

The next step of the process is "oscillation" (repeated injection and aspiration of MTBE). The amount of liquid to be oscillated is first selected, the number of seconds is set on the seconds remaining counter 274, and an appropriate oscillation frequency is chosen by manipulating flow controls 132 and 298. Preferably the entire amount infused can be oscillated, but usually less than the entire amount infused is selected for oscillation. For instance, from 1.0 to 7.0 milliliters of MTBE can be selected for oscillation. With multiple infusions, any desirable volume can be selected for oscillation into the gallbladder. The period of treatment can extend over several days, if desired.

Oscillation is selected by toggling switch 156 on the front of the pump. With the valves in home position, the bellows repeatedly extends and compresses to agitate the selected amount of fluid to and from the gallbladder for the selected number of seconds. This is accomplished by the air logic system 9 as explained above.

Should the system need to be stopped, stop button 160 is pressed, which returns everything to home position. Problems can then be handled, fresh MTBE can be added to the reservoir, or the like.

When oscillation is complete, the withdraw cycle is manually initially, either because the entire procedure is complete or because a fresh aliquot of MTBE is desired. Withdraw toggle 162 on the front of the pump is hand-activated and all of the fluid is withdrawn from the system into the main reservoir, controlled by the air logic system as described above. Basically, the vacuum pump is activated, and reservoir syringe 17 thereby caused to aspirate all the liquid in the system into the reservoir 16. Bile being heavier than the solvent, quickly separates and settles to the bottom so that upon each reinfusion largely fresh MTBE is injected.

When the seconds programmed on the seconds remaining counter 139 have expired, the operator initiates a withdraw. Pinch valves 12 and 13 open and a vacuum is generated in the vacuum chamber 18 surrounding the plunger 63 of the reservoir syringe 17. The open pinch valves allow direct fluid communication between the gallbladder and the reservoir 16. The vacuum then draws the syringe plunger 63 out so that the contents of the gallbladder are aspirated into the bellows. Bile, the heavier phase, separates at the bottom of the bellows from which it is naturally extracted first into the reservoir syringe. If desired, for instance if the solvent has become saturated with solute, an entirely new reservoir syringe can be inserted and filled before the next infusion.

Alternatively, as described above, saturated solvent can be emptied from the reservoir into the waste bottle 137 and a fresh aliquot of solvent can be drawn into the reservoir from bottle 72 and hence into the gallbladder as many times as is desired.

In addition, the location of the bellows can be monitored by the user manually rotating position switch 99 either left to empty or right to fill the reservoir 16. The pneumatic logic necessary to perform this operation is shown schematically on FIG. 2.

To fill the reservoir 16, a fluid channel is opened between supply bottle 72 and said reservoir 16, by opening pneumatically controlled pinch valve 98. (Pinch valves 98 and 97 operate as is described above with reference to pinch valves 12 and 13.) A vacuum generated in vacuum chamber 18 causes plunger 63 of syringe 17 to be withdrawn and thus extract fresh solvent from bottle 72 via tubing 75. Air may enter bottle 72 to replace the solvent removed via sterile filter 94 located in bottle cap 75. Upon release of switch 99 pinch valve 98 closes and vacuum chamber 18 is vented to the atmosphere.

To empty reservoir 16, valve 99 is rotated to the "fill" position causing pinch valve 97 to open and a vacuum to occur in waste bottle 137. Spent solvent and bile is transferred under vacuum via tube 95 out of reservoir 16 and into waste bottle 137. Upon release by the user, valve 99 automatically returns to its off position so that pinch valve 97 closes and waste bottle 137 is vented to atmospheric pressure. Float valve 135 prevents accidental overfilling of waste bottle 137, (which would permit solvent to enter the logic circuit). As the fluid level in bottle 137 increases, float ball 131, being buoyant, rises as well and flexible tube 133 is bent by this action at a pre-pressed bend spot 150 until it occludes and prevents flow through the tube. Thus, any further attempts to draw fluid into waste bottle 137 are prevented until empty replacement for bottle 137 is attached. Bottle 137 is preferably sized to hold a complete day's worth of waste solvent before reaching its capacity.

Finally, if the entire dissolution process is completed (which is determined by reinjecting imaging solution into the gallbladder via syringe 10), the withdraw cycle is the last stage of the process. The catheter is then removed from the pump and from the patient, now happily free of gallstones dissolved by the above process.

What is claimed is:

1. A pumping apparatus for pumping preselected volumes of fluid through a catheter means insertable into a fluid receiving body such as a human gallbladder, said pumping apparatus comprising:
  a syringe means fluidly connectable to a fluid source;
  a means for withdrawing a preselected volume of fluid into said syringe means;
  a flexible bellows fluidly connected to said syringe means and connectable to said catheter means such that alternate compression and extension of said bellows may be employed to transfer fluid back and forth between syringe means and said catheter means;
  a programmable controller operatively connected to said pumping apparatus to control the frequency and numerosity of fluid transfers back and forth between said syringe means and said catheter means.

2. The apparatus of claim 1 wherein said means for withdrawing a preselected volume of fluid into said syringe means comprises:
  (a) a chamber sealably mounted on at least a portion of said syringe means such that creation of a vacuum within said chamber will cause withdrawal of fluid into said syringe means; and
  (b) a vacuum source connected to said chamber to create a vacuum therein.

3. The apparatus of claim 2 further comprising:
  a first valve for alternately opening and closing the fluidic connection between said syringe means and said fluid source;
  a second valve for alternately opening and closing the fluidic connection between said syringe means and said bellows.

4. The apparatus of claim 3 wherein:
  said controller is operatively connected to (a) said bellows, (b) said first valve, (c) said second valve and (d) said vacuum source; and
  said controller is programmed to:
    i. open said first valve and close second valve;
    ii. cause said vacuum source to withdraw fluid from said fluid source into said syringe; and, thereafter
    iii. close said first valve and open said second valve to permit fluid from said syringe to be infused through said bellows and through said catheter.

5. The apparatus of claim 2 wherein said vacuum source comprises a Bernouilli's valve.

6. The apparatus of claim 1 wherein said flexible bellows comprises:
  a flexible bellows member sealably positioned between first and second rigid cap means and having a movable bellows drive piston connected to at least one of said rigid cap means to alternately compress and expand said bellows, the length of the stroke of said piston being adjustable to permit adjustment of the volume of fluid to be transferred by each compression and expansion of said bellows.

7. The apparatus of claim 1 further comprising:
  a first valve for alternately opening and closing the fluidic connection between said syringe means and said fluid source;
  a second valve for alternately opening and closing the fluidic connection between said syringe means and said bellows.

8. The apparatus of claim 7 wherein:
  said controller is operatively connected to (a) said bellows, (b) said first valve and (c) said second valve; and
  said controller is programmed to initially open said first valve and close said second valve to allow withdrawal of fluid from said fluid source into said syringe and to thereafter close said first valve and open said second valve to permit infusion of fluid from said syringe through said bellows and into said catheter.

9. The apparatus of claim 7 further comprising:
  a third valve for alternately opening and closing the fluidic connection between said bellows and said catheter means.

10. The apparatus of claim 9 wherein:
  said controller is operatively connected to (a) said second valve, (b) said third valve and (c) said bellows; and
  said controller is programmed to alternately open and close said first and second valves and to alternately compress and expand said bellows in relative relation to the opening and closing of said first and second valves to thereby withdraw fluid from said fluid receiving body through said catheter means to said bellows and to pump said withdrawn fluid from said bellows into said syringe means.

11. The apparatus of claim 7 wherein:
  said controller is operatively connected to (a) said first valve, (b) said second valve and (c) said bellows; and
  said controller is programmed to:
    i. close said first valve;
    ii. open said second valve;
    iii. repeatedly expand and compress said bellows to effect oscillatory movement of fluid back and forth through said catheter means.

12. The apparatus of claim 7 wherein the first valve and second valve opposite pinch valves.

13. The apparatus of claim 1 wherein said controller is operatively connected to said bellows and is programmable to effect programmed changes in the volume of fluid being pumped by said bellows.

14. The apparatus of claim 1 wherein the volumetric capacity of said bellows is adjustable to cause 1.0 to 7.0 milliliters of fluid to oscillate back and forth through said catheter means.

15. The apparatus of claim 1 further in combination with said catheter means, and wherein said catheter means is a pigtail catheter.

16. The apparatus of claim 1 wherein:
  said bellows is disposed in a generally vertical orientation such that it will expand and contract in a generally vertical direction; and
  a top fluidic connection port being formed in the top said bellows and a bottom fluidic connection port being formed in the bottom of said bellows.

17. The apparatus of claim 59 wherein:
  the top fluidic connection port is connectable to the catheter means; and,
  the bottom fluidic connection port is connected to the syringe member;
  said bellows being thereby operative to differentially pump a two-phase liquid contained therein such that the upper phase of said liquid will be expelled through said top port and into said catheter and the lower phase of said liquid will be expelled through said bottom port and into said syringe.

18. The apparatus of claim 1 wherein the volumetric capacity of said bellows ranges from 0.5 to 20 milliliters.

19. The apparatus of claim 1 wherein said bellows further comprises a means for manually adjusting the volumetric capacity of said bellows between the range of about 0.5 to 20 milliliters.

20. The apparatus of claim 1 further comprising a waste container fluidly connected to said apparatus such that waste fluid may be withdrawn through said catheter means and expelled directly into said waste container.

21. The apparatus of claim 1 wherein said syringe comprises a plunger element slidably disposed within a barrel element and wherein said means for withdrawing a preselected volume of liquid into said syringe further comprises:
- a sealed vacuum chamber formed about at least a portion of said syringe such that the formation of negative pressure within said chamber will cause the plunger of the syringe to withdraw within the syringe barrel; and
- a negative pressure source connectable to said chamber to thereby evoke withdrawal of the plunger of said syringe within the barrel of said syringe.

22. The apparatus of claim 1 further comprising:
- a second syringe attached to the fluidic interconnection between said bellows and said catheter to permit air to be purged from fluid passing from said bellows to said catheter.

23. An apparatus for effecting in situ infusion and extraction of dissolution fluid into and out of a human gallbladder, said device comprising:
- a dissolution fluid container;
- a syringe pump fluidly connected to said dissolution fluid container;
- a bellows pump fluidly connected to said syringe pump;
- a catheter insertable into the gallbladder and fluidly connected to said bellows pump;
- a first valve for opening and closing the fluidic connection between said dissolution fluid container and said syringe pump;
- a second valve for opening and closing the fluidic connection between said syringe pump and said bellows pump;
- a third valve for opening and closing the fluidic connection between said bellows pump and said catheter; and
- a programmable logic controller operatively connected to (a) said first valve, (b) said second valve, (c) said third valve, (d) said syringe pump and (e) said bellows pump, said controller being programmed to:
  i. open said first valve and close second valve;
  ii. cause said syringe pump to withdraw dissolution fluid from said dissolution fluid container into said syringe pump;
  iii. close said first valve; and
  iv. alternately open and close said second and third valves while expanding and contracting said bellows relative to the opening and closing of said second and third valves so as to pump dissolution fluid from said syringe pump through said bellows and through said catheter;
  v. close said second valve, open said third valve and repeatedly expand and contract said bellows to effect oscillatory back and forth movement of dissolution fluid through said catheter;
  vi. open said second and third valve and cause said syringe pump to withdraw the dissolution fluid through said catheter through said bellows and into said syringe pump.

24. The apparatus of claim 23 further comprising a waste receptacle fluidly connected to said syringe pump and wherein said programmable controller is further programmed to:
  vii. close at least said second valve; and
  viii. cause said syringe pump to expel the withdrawn dissolution fluid from said syringe pump into said waste container.

25. The apparatus of claim 24 further comprising a float valve positioned within said waste receptacle to prevent over filling of said waste receptacle.

26. The apparatus of claim 23 further comprising:
- a stopcock positioned in the fluid connection between said bellows and said catheter to permit bleed-off of air and excess fluid.

27. The apparatus of claim 26 wherein a syringe is attached to said stopcock positioned in the fluid connection between said bellows and said catheter such that said syringe may be utilized to draw a quantity of dissolution fluid from said syringe pump through said bellows and into said syringe, thereby effecting priming of at least said bellows pump.

28. The apparatus of claim 23 wherein said syringe pump comprises:
- a syringe having a barrel portion and a plunger portion;
- a chamber sealably mounted on at least a portion of said syringe such that creation of a vacuum within said chamber will cause the plunger of the syringe to withdraw within the syringe barrel; and
- a vacuum source for creating a vacuum within said air-tight housing to cause withdrawal of the syringe plunger in the syringe barrel.

29. The apparatus of claim 28 further comprising a positive pressure source attached to said air-tight housing to create positive pressure therein to cause forward advancement of the syringe plunger within the syringe barrel.

30. The apparatus of claim 28 wherein the barrel of said syringe comprises an inner bore wherein the plunger of said syringe is slidably received and wherein at least a portion of said plunger is of reduced diameter relative to the bore of the barrel thereby minimizing the tendency of the piston to become immobilized relative to the barrel.

31. The apparatus of claim 23 wherein said bellows comprises:
- a flexible bellows member sealably positioned between first and second rigid cap means and having a movable bellows drive piston connectable to at least one of said rigid cap means so as to alternately compress and expand said bellows, the length of the piston stroke being adjustable to permit a selected volume of fluid to be transferred by each compression and expansion of said bellows.

32. The apparatus of claim 23 wherein said controller comprises a programmable pneumatic controller.

33. The apparatus of claim 23 wherein said catheter comprises a pigtail catheter.

34. The apparatus of claim 23 wherein said first, second and third valves comprise pneumatically actuatable pinch valves.

35. The apparatus of claim 23 wherein said bellows further comprises means for manually adjusting the volumetric capacity of said bellows between the range of about 0.5 to 20 milliliters.

* * * * *